(12) United States Patent
Gillespie, III

(10) Patent No.: US 6,387,078 B1
(45) Date of Patent: May 14, 2002

(54) AUTOMATIC MIXING AND INJECTING APPARATUS

(76) Inventor: Richard D. Gillespie, III, 6136 FM 1616, Athens, TX (US) 75761

( * ) Notice: Subject to any disclaimer, the term of this patent is extended or adjusted under 35 U.S.C. 154(b) by 0 days.

(21) Appl. No.: 09/745,905

(22) Filed: Dec. 21, 2000

(51) Int. Cl.⁷ .............................................. A61M 5/00
(52) U.S. Cl. ...................... 604/181; 604/187; 604/201; 604/264
(58) Field of Search .................... 604/181, 187, 604/191, 201, 203, 205, 264, 272, 86, 87, 88, 89

(56) References Cited

U.S. PATENT DOCUMENTS

| | | | |
|---|---|---|---|
| 4,755,169 A | 7/1988 | Sarnoff et al. | 604/51 |
| 4,820,286 A | 4/1989 | van der Wal | 604/89 |
| 4,822,340 A | 4/1989 | Kamstra | 604/135 |
| 4,969,877 A | 11/1990 | Kornberg | 604/195 |
| 5,085,642 A | 2/1992 | Sarnoff et al. | 604/134 |
| 5,092,843 A | 3/1992 | Monroe et al. | 604/138 |
| 5,102,393 A | 4/1992 | Sarnoff et al. | 604/136 |
| 5,295,965 A | 3/1994 | Wilmot | 604/136 |
| 5,300,030 A | 4/1994 | Crossman et al. | 604/136 |
| 5,358,489 A | 10/1994 | Wyrick | 604/136 |
| 5,540,664 A | 7/1996 | Wyrick | 604/136 |
| 5,620,421 A | 4/1997 | Schmitz | 604/135 |
| 5,665,071 A | 9/1997 | Wyrick | 604/134 |
| 5,685,846 A | * 11/1997 | Michaels, Jr. | 604/90 |
| 5,695,472 A | 12/1997 | Wyrick | 604/136 |
| RE35,986 E | * 12/1998 | Ritson et al. | 604/88 |

* cited by examiner

*Primary Examiner*—Brian L. Casler
*Assistant Examiner*—Kevin C. Sirmons
(74) *Attorney, Agent, or Firm*—John A. Thomas

(57) ABSTRACT

An automatic mixing and injecting apparatus comprises a syringe assembly within a housing. The syringe assembly has a chamber for holding a liquid, which can be a liquid medicine or a solvent. A second chamber may hold a dry medicine. The second chamber is releasably sealed with respect to the first chamber. A spring-operated plunger forces liquid from the first chamber and causes the releasable seal to disengage when the needle has entered the recipient. At this time, the liquid flows through the second chamber and dissolves any dry medicine in that chamber. A releasable coupling disengages the plunger from the driver spring and allows the plunger, syringe, and needle to retract under the urging of a return spring.

19 Claims, 9 Drawing Sheets

AUTOMATIC MIXING AND INJECTING APPARATUS

BACKGROUND OF THE INVENTION

The present invention relates to devices pre-loaded with a medicine and intended to automatically administer a predetermined dose of a liquid medicine by means of an intramuscular, subcutaneous or transdermal injection. In particular, the present invention incorporates a number of important improvements and features as compared to the prior art, including enhanced functionality, convenience, safety and versatility. The present invention also provides a means for quickly administering a pre-determined dose of medication when a need for rapid emergency treatment arises. The present invention may be embodied in a device that can be easily, safely and conveniently carried on the person. The present invention allows a single embodiment that may administer a liquid medicine alone or, alternatively, allow a liquid solvent to automatically mix with a dry medicine upon actuation of the device and concurrent with the injection process. The preferred embodiment automatically renders itself safe for disposal after use and eliminates the risk of injury to others through inadvertent contact with the used hypodermic needle. The recipient before, during, or after the injection, need not even see the hypodermic needle.

The use of automatic injection devices has been primarily reserved to emergency, life-sustaining situations. Additional applications for the present invention would be instances where the anatomical site of the injection, such as the penis, make the functional and psychological benefits associated with the use of such a device worth the added cost as compared to the conventional syringes.

There are numerous embodiments of automatic injection apparatuses in the prior art, e.g. Wyrick, U.S. Pat. No. 5,665,071; Schmitz, U.S. Pat. No. 5,620,421; and Wilmot, U.S. Pat. No. 5,295,965. None of the prior art patents provide all of the benefits of the present invention, however.

SUMMARY OF THE INVENTION

The present invention pertains to an automatic injection apparatus which injects a single, pre-measured dose of stored medicine intramuscularly or transdermally, and which automatically retracts the hypodermic needle into the device after the injection is completed. In the preferred embodiment, the medicine may comprise either a preprepared liquid medicine, a liquid solute that is forced through a dry drug chamber where a soluble medicine is mixed with the solute and carried in solution into the recipient, or a combination of a liquid medicine that also serves as a solute for a dry drug that mixes upon injection.

The preferred embodiment resembles a permanent marker pen. It has an actuation end and a needle end. For the purposes of this application, the actuation end of the device will be referred to as the proximal end of the device and the needle end will be referred to as the distal end. A removable cap preferably covers the proximal end of the device to protect against accidental actuation. The user presses the distal end of the device onto the desired injection site and presses the actuation button. This releases the plunger and syringe combination from its temporary engagement with the housing. The plunger and syringe combination is then forced away from the proximal end of the housing by a energized driver spring. The driver spring propels the plunger and syringe combination forward through the bore of the housing until the hypodermic needle exits the housing, and enters the recipient's tissue. During this movement, a return spring positioned between the syringe assembly and the fixed, distal end of the housing becomes compressed and energized. Once the plunger and syringe combination comes to rest against the impact damper pad at the distal end of the housing, the syringe assembly remains stationary and the plunger begins to move axially forward relative to the syringe. As the plunger moves forward, the pressure within the liquid within the syringe begins to rise rapidly until it reaches a critical threshold pressure. Upon reaching the threshold pressure, a rigid disk separating the first liquid chamber from the second dry drug chamber disengages from a circumferential seal holding it into place relative to the syringe. Once separated from the circumferential seal, the disk moves forward until it comes to rest against a retaining surface in the dry drug chamber and the liquid flows through apertures around the disk and into the dry drug chamber.

If the dry drug chamber contains a dry medicine, the dry medicine is drawn into solution by the liquid as the plunger continues its forward movement and the liquid is forced through the dry drug compartment and into the entrance to the hypodermic needle. Otherwise, the liquid medicine flows through the same chamber and continues on into the recipient. When the liquid is discharged, the coupling that engages the driver spring and the plunger comes into contact with a splitter which disengages the driver spring from the plunger. Without the influence of the driver spring upon the plunger and syringe combination, the energized return spring forces the plunger and syringe combination to retreat rearward towards the proximal end of the device until the hypodermic needle is fully retracted into the housing.

In general, the preferred embodiment comprises a housing having a cavity and a proximal and a distal end. A syringe assembly is located within the housing cavity, and the syringe assembly further comprises a first chamber for holding a liquid; a second chamber for holding a dry medicine (the second chamber disposed distally to the first chamber); a disk releasably sealing the first chamber from the second chamber; a needle, (the needle disposed distally of the second chamber); a plunger having a plunger shaft disposed proximally; and, at least one aperture in the wall of the second chamber allowing liquid communication between the portion of the second chamber proximal to the released disk and the portion of the second chamber distal to the released disk, so that the liquid flows through the second chamber before being forced through the needle. The plunger operates to force the liquid from the first chamber into the second chamber.

A driver spring is located within the housing. The driver spring engages the plunger shaft, and operates, when released, to inject the needle and displace the liquid from the first chamber, through the second chamber and through the needle. A spring-top-plunger coupling engages the plunger shaft and the driver spring. A splitter is attached to the housing distally to the spring-to-plunger coupling. The splitter has a surface for engaging the spring-to-plunger coupling and forcing the spring-to-plunger coupling to disengage from the plunger shaft, thereby disengaging the driver spring from the syringe assembly.

The driver spring is disengaged by opening of the spring-to-plunger coupling. The plunger shaft has a circumferential groove; and, the spring-to-plunger coupling has a plurality of axial slits and a radial lip for releasably engaging the circumferential groove. Thus, the radial lip disengages from the circumferential groove as the spring-to-plunger coupling engages the splitter, and the spring-to-plunger coupling is forced open.

The plunger shaft has at least two compressible barbs connected to its proximal end. An actuation rod is axially moveable within the housing. The rod has an interior bore sized to receive the barbs in their compressed state. The housing has a detent sized to engage the barbs in their uncompressed state and prevent the distal movement of the plunger shaft until the barbs are compressed.

A return spring is disposed between the housing and the syringe assembly, and urges the syringe assembly proximally.

The preferred embodiment has a flexible septum disposed proximally to the proximal end of the needle and sealing the needle from the second chamber, so that liquid pressure in the second chamber causes the septum to deflect distally until it is penetrated by the proximal end of the needle.

DETAILED DESCRIPTION OF THE PREFERRED EMBODIMENT

It is important to note that although the following description will be defined in the context of the example of the preferred embodiment, this is for illustrative purposes only. The invention is not so limited and is applicable to all other embodiments as allowed by the claims.

Figure 1:
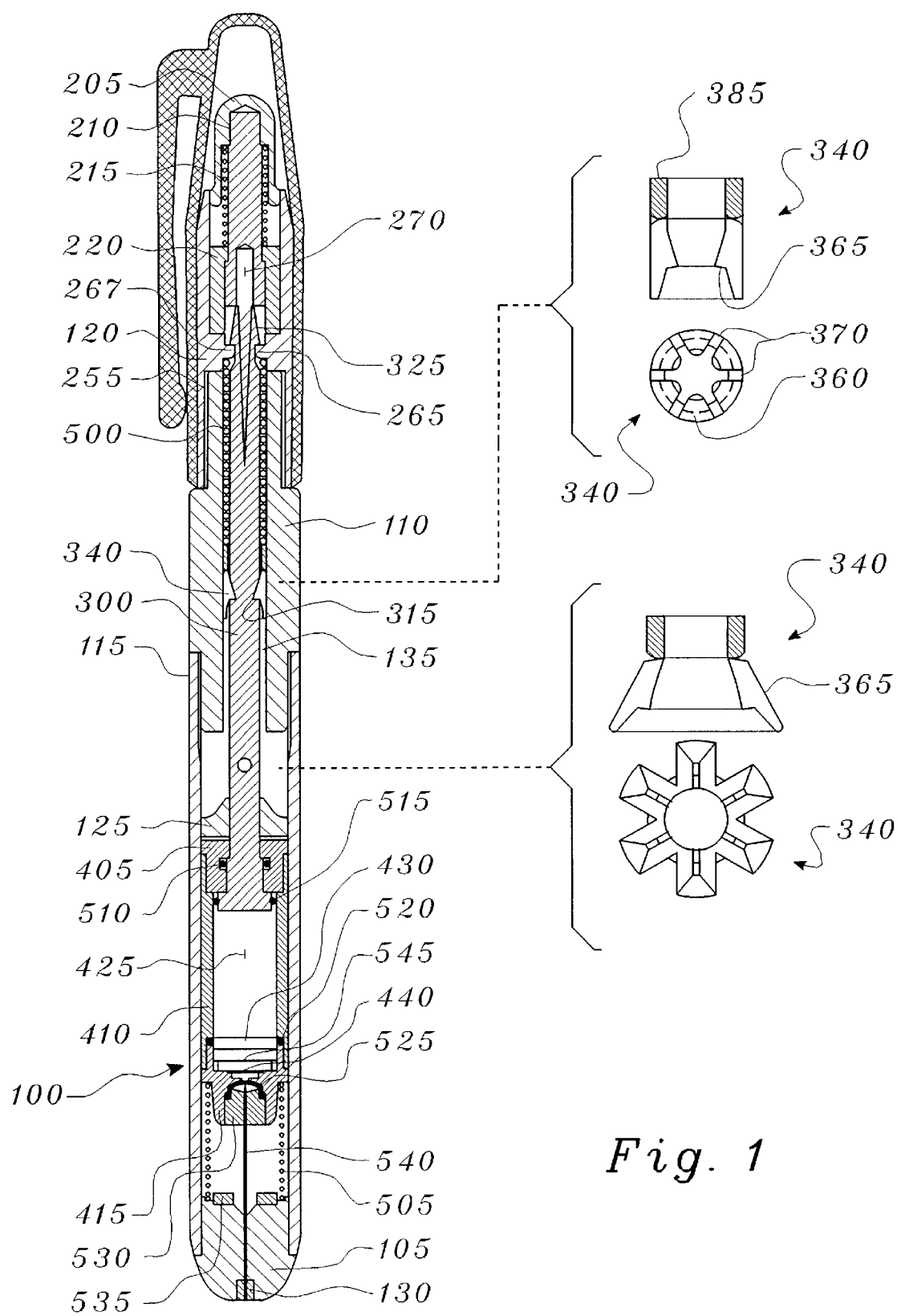
FIG. 1 is a cross-sectional view of a preferred embodiment of the preferred embodiment in a state of readiness.
Figure 2A:
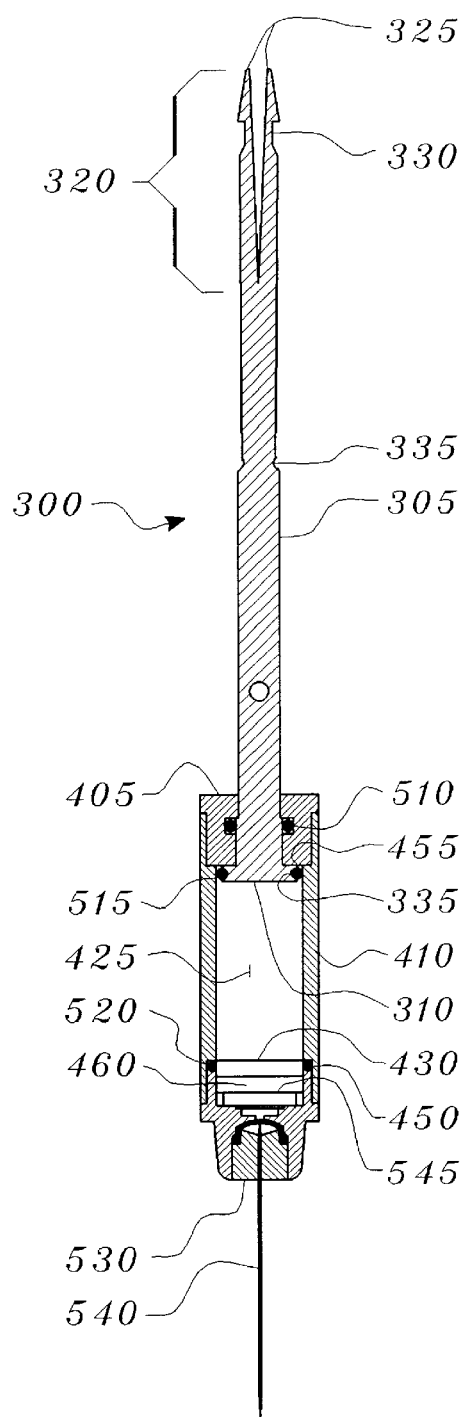
FIG. 2 provides additional details of the Housing and plunger, syringe, and needle assemblies.
Figure 2B:
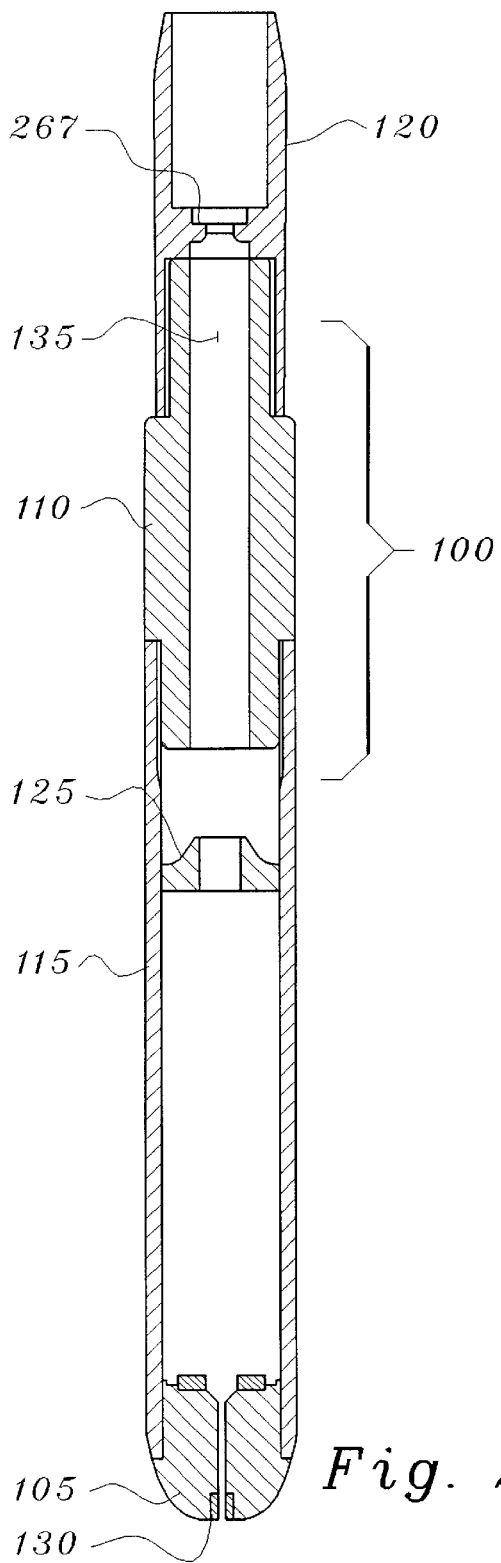

FIG. 1 shows a cross section of the preferred embodiment of the automatic mixing and injecting apparatus. In this application, "the proximal end" of the apparatus is the end having the actuation button (205), and the "distal end" is the end of the apparatus having the needle (540). The preferred embodiment preferably has a removable cap for preventing accidental triggering, an actuation button (205), an actuation button rod (210), an actuation button return spring (215), an actuation button retainer cap (220), a housing cap (120), a driver spring (500), a spring-to-plunger coupling (340), a housing midsection (110), a plunger (300), a housing tubular section (115), a coupling splitter (125), an upper syringe cap (405), an upper syringe cap seal (510), a plunger seal (515), a liquid medicine, diluent, or solvent, (collectively called "a liquid" (425) hereafter); a syringe barrel (410), a rupture disk (430), a rupture disk seal (520), an optional dry, or lyophilized, medicine (545), a filter (440), a drug chamber lower seal (525), a lower syringe cap (415), a needle hub (530), a needle (540), a syringe return spring (505), an impact damper pad (535), a housing nose (105), and a needle point seal (130). FIG. 2 shows the housing (100), which comprises the housing cap (120), housing midsection (110), housing tubular section (115), and the housing nose (105), which are all permanently joined by means of threaded or bonded connections to form the housing (100).

Figures 3A, 3B:
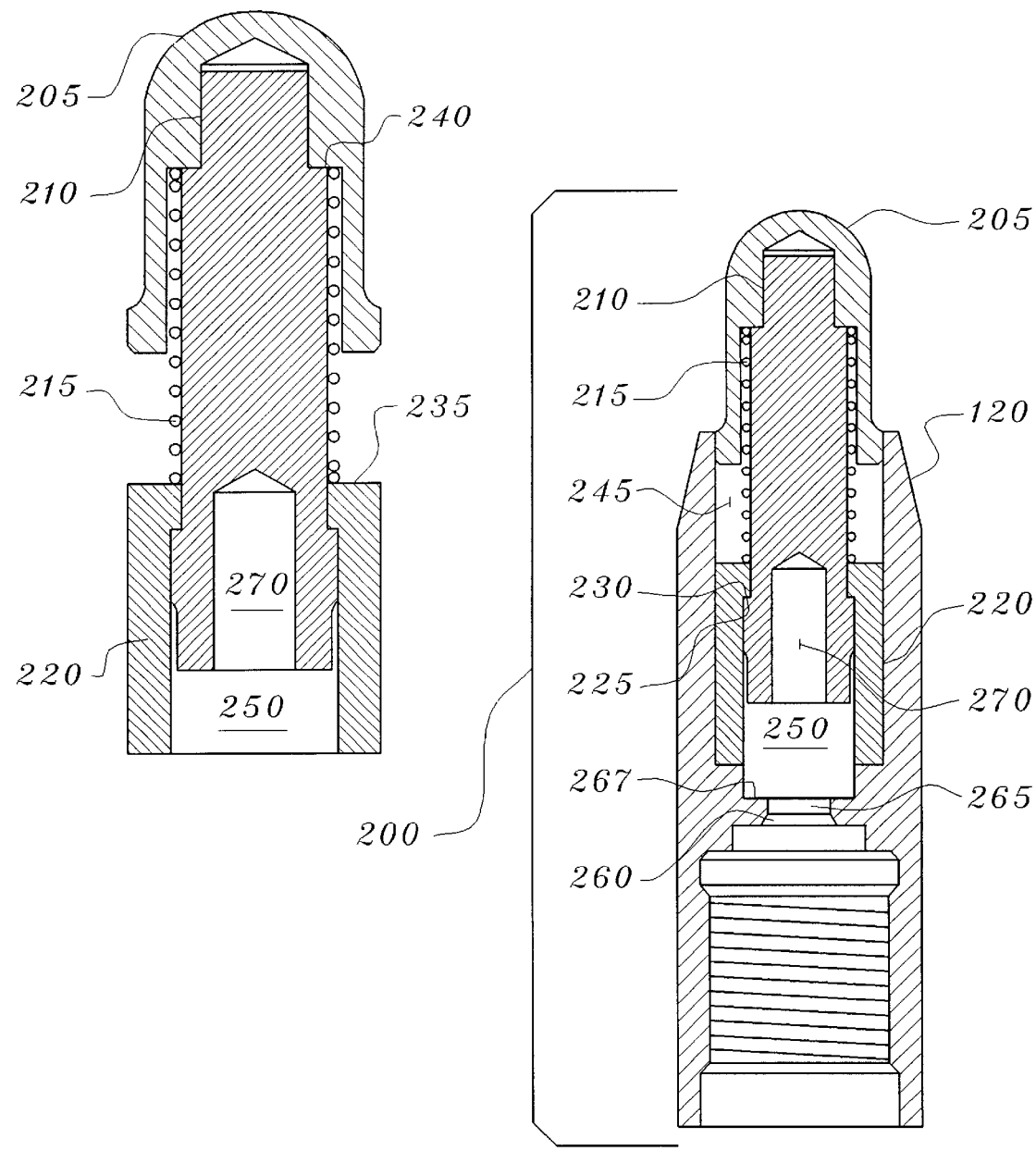
FIG. 3 provides additional details of the actuation button assembly.

Referring to FIG. 3, elements (205), (210), (215), (220) and (120) form a permanently assembled actuation button assembly (200). During assembly of the actuation button assembly (200), the actuation button rod (210) enters into axial engagement with the actuation button retainer cap (220) from the distal end of actuation button retainer cap (220). The actuation button rod (210) slidably cooperates with the actuation button retainer cap (220). An exterior radial shoulder (225) exists on the actuation button rod (210) that denotes a sharp reduction in outside diameter. This shoulder cooperates with a radial shoulder (230) that is interior to the actuation button retainer cap (220) and that defines a transition between the major and minor interior diameters of the actuation button retainer cap (220). The actuation button rod exterior radial shoulder (225) abuts against the actuation button retainer cap (220) interior radial shoulder (230) under the influence of the actuation button return spring (215). This limits the axial travel of the actuation button toward the proximal end of the device.

After the actuation button rod (210) is assembled with the actuation button retainer cap (220), the actuation button return spring (215) slides over the outside of the actuation button rod (210) from the proximal end and rests against the proximal face (235) of the actuation button retainer cap (220). The actuation button (205) is then permanently affixed, preferably by means of press fit, onto the actuation button rod (210). The actuation button return spring (215) is thus captured in a state of minor compression with its distal end resting upon the proximal face (235) of the actuation button retainer cap (220) and the proximal end resting against the interior shoulder (240) of the actuation button (205). After completing the assembly of these elements (205), (210), (215) and (220), the assembly is then permanently assembled, preferably by means of an interference fit, into the proximal end of the housing cap (120).

Following assembly with the housing cap (120), the actuation button (205) slidably cooperates with the interior bore (245) of the housing cap (120) and the actuation button rod (210) slidably cooperates with the interior bore (250) of the actuation button retainer cap (220). When the actuation button (205) is moved axially relative to the housing cap (120) toward the distal end, the actuation button return spring (215) compresses and stores energy. When force against the actuation button (205) is released, the energy stored in the actuation button return spring (215) returns the actuation button (205) and actuation button rod (210) back to a preferred position where the actuation button (205) is extended beyond the proximal end of the housing cap (120) and the shoulder interior radial shoulder of the actuation button rod (210) rests against the interior radial shoulder (230) of the actuation button retainer cap (220).

As shown in FIG. 1, a driver spring (500) is shown in a fully compressed state. The proximal end of the compressed driver spring (500) rests against an interior face (255) of the housing cap (120). The opposite end of the compressed driver spring (500) rests against the proximal surface (385) of the spring-to-plunger coupling (340). In the preferred embodiment, the driver spring (500) stores mechanical energy, and provides an adequate amount of axial extension, to move, upon actuation of the device, the spring-to-plunger coupling (340), and the plunger (300) with which the spring-to-plunger coupling (340) is engaged, axially towards the distal end of the device. This axial movement continues until the spring-to-plunger coupling (340) contacts, and is spread radially by the coupling splitter (125). In the preferred embodiment, the driver spring (500) retains a residual compressive force at the end of its extension. The driver spring (500) and the spring-to-plunger coupling (340) slidably cooperate with the interior bore (135) of the housing midsection (110).

The spring-to-plunger coupling (340) is captured radially between the interior bore (135) of the housing midsection (110) and a circumferential groove (315) of the plunger (300). In the preferred embodiment, the circumferential groove (315) around the plunger (300) accepts a correspondingly shaped radial lip (365) on the interior of the spring-to-plunger coupling (340) that allows the compression force of the driver spring (500) applied to the spring-to-plunger coupling (340) to be transmitted axially to the plunger (300). During assembly, the end of the plunger (300) having the barbs (325) is orientated towards the proximal end of the device. The driver spring (500) is then compressed axially between the housing cap (120) and the spring-to-plunger coupling (340), while being captured within the interior bore (135) of the housing midsection (110). This axial compression continues until the end of the plunger (300) having the barbs (325) contacts the tapered interior surface (260) of the housing cap (120). The plunger (300) of the preferred embodiment is fabricated of a resilient material, which may be metal or plastic, and therefore possesses the capacity for elastic deformation in the barbed region (320). Upon continued compression of the driver spring, the barbs (325) collapse together and pass through an aperture (265) in the housing cap (120) at which time they are elastically deformed. Upon additional compression of the driver spring (500) and further passage of the elastically deformed plunger barbs (325) through the aperture (265) of the housing cap (120), the barbs (325) eventually exit the constraining surface of the housing cap aperture (265). Upon exiting the aperture (265) in a proximal direction, the elastic property of the barbed region (320) allows it to return to its original shape. In the preferred embodiment, the inside diameter of the aperture (265) in the housing cap (120) is slightly smaller than the free distance at the neck (330) of the plunger barbs (325). This insures that the neck (330) of the plunger (300) remains in contact with the aperture surfaces (265) of the housing cap (120), thus insuring the plunger (300) remains centered within the aperture (265) of the housing cap (120) during the device's state of readiness. Once the barbs (325) of the plunger (300) passes through the aperture (265) of the housing cap (120), the driver spring (500) remains in a state of full compression until the actuation button (205) is physically forced towards the distal end of the device.

Figure 4:
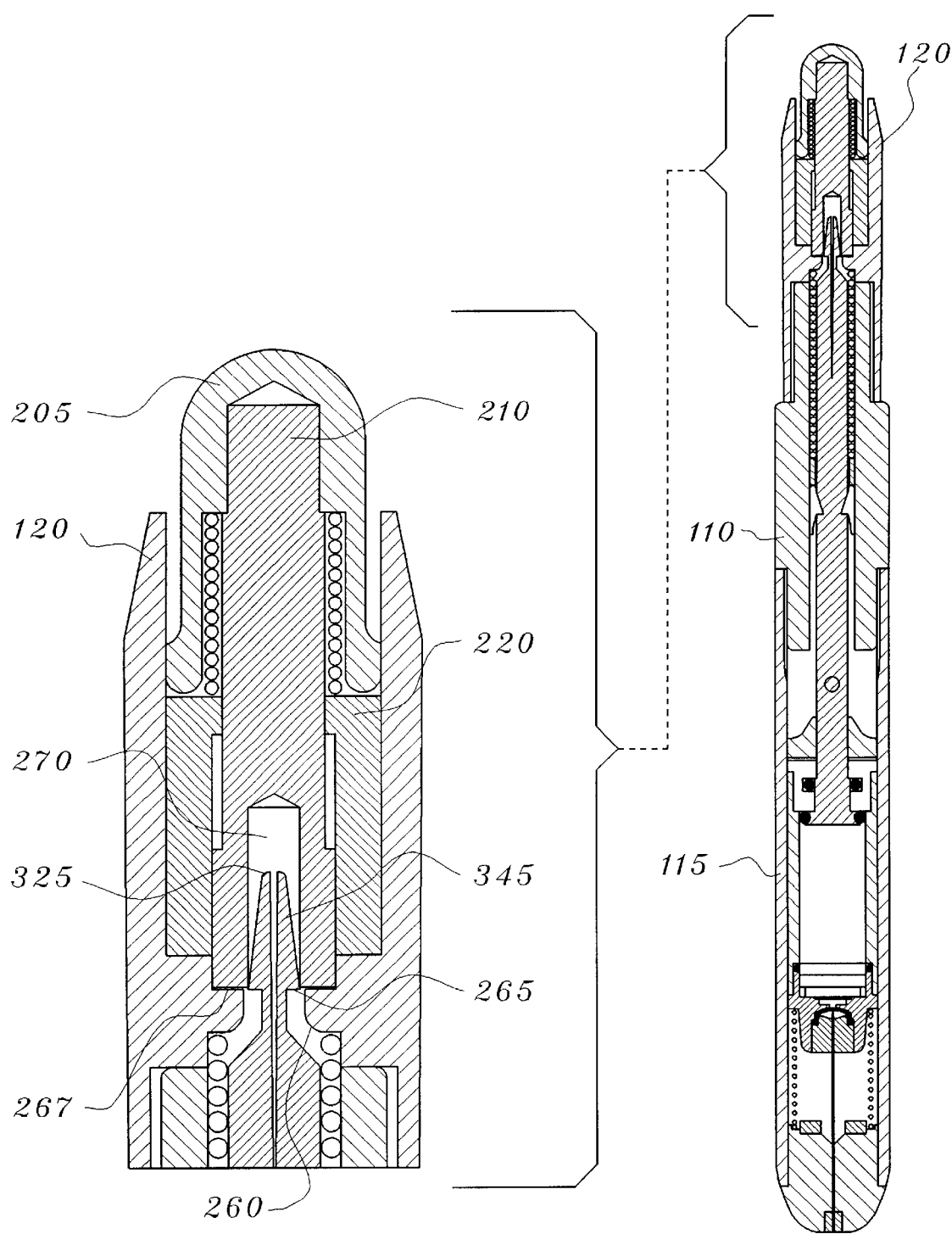
FIG. 4 describes the device, as the actuation button is compressed and just prior to the initial forward movement of the plunger, syringe, and needle assembly.

Referring to FIG. 4, as the user pushes the actuation button (205) towards the distal end of the device, the interior bore (270) of the actuation button rod (210) engages the tapered surface (345) of the plunger barbs (325). Upon continued movement of the actuation button (205), the actuation button rod (210) collects the barbs (325) within the interior bore (270) of the actuation button rod (210), defeating the natural elastic property of the plunger barbed region (320). As the actuation button (205) approaches the limit of its travel in the distal direction, the plunger barbed region (320) is forced together until an interference with the aperture (265) no longer exists. Once the plunger barbs (325) compress and the interference condition between the plunger barbs (325) and the housing cap (120) is eliminated, the fully compressed and energized driver spring (500) is no longer constrained from extending in the distal direction. The driver spring extends and forces the plunger towards the distal end of the device by virtue of the circumferential engagement between the plunger (300) and the spring-to-plunger coupling (340) on which the driver spring (500) acts.

As shown in FIG. 2, the plunger (300) has barbs (325), a long cylindrical shaft (305) into which a circumferential groove (315) is machined, and a face (310). The barbs (325) have been previously described. The circumferential groove (315) machined around the periphery of the long cylindrical shaft (305) receives the internally directed radial lip (365) on the interior of the spring-to-plunger coupling (340) as previously described. A circumferential groove (335) is machined about the periphery of the face (310) of the plunger (300). This groove is fitted with an elastomeric plunger seal (515) that resides in contact with, and within the interior confines of, a syringe barrel (410). The plunger seal (515) resides in a state of minor compression between the syringe barrel (410) and the circumferential groove (335) of the face of the plunger (300), and slidably cooperates with the interior surface (420) of the syringe barrel (410). The plunger seal (515) is intended to prevent leakage of the liquid (425) past the plunger (300) as the pressure within the syringe barrel (410) increases. In the preferred embodiment, surfaces of the syringe barrel (410) and plunger (300) that are exposed to direct contact with the liquid (425) would be fabricated of, or coated with, inactive materials which are benign to the human body and are non-reactive with the liquid.

In the preferred embodiment, the syringe barrel (410) is permanently bonded to an upper syringe cap (405). An upper syringe cap seal (510) resides within an interior circumferential groove (445) of the upper syringe cap (405) and resides in a state of compression while resting against the periphery of the plunger (300). At the distal end of the syringe barrel (410), an elastomeric rupture disk seal (520) resides within a cylindrical counterbored pocket (450) where the rupture disk seal (520) makes circumferential and flat contact with the cylindrical counterbored pocket (450) of the syringe barrel.

The flat contact prevents movement of the disk seal (520) if a force in the axial direction towards the proximal end of the device is imposed on the rupture disk seal (520). The inside diameter of the circumferential pocket (450) of the syringe barrel (410) is slightly smaller than the outside diameter of the rupture disk seal (520). The elastomeric rupture disk seal (520) is thus compressed when installed into the counterbored pocket (450) of the syringe barrel (410) and forms a liquid tight seal which prevents the liquid (425) from leaking between the contacting surfaces.

During assembly, the syringe barrel (410) and upper syringe cap (405) are permanently joined, preferably by means of an interference fit. The upper syringe cap seal (510) is then installed in the upper syringe cap (405). The plunger (300) and the plunger seal (515) are then assembled with the syringe barrel (410) and the upper syringe cap (405) with the barbs (325) of the plunger (300) entering the syringe barrel (410) from the distal end of the syringe barrel (410). The plunger (300), then moves axially towards the proximal end of the syringe assembly until the plunger (300), abuts against the inside flat surface (455) of the upper syringe cap (405). This condition represents the relationship that exists between the plunger (300) and the syringe assembly (400) when the device is assembled and in a state of readiness for use.

Once the plunger (300), the syringe barrel (410) and the upper syringe cap (405) have been assembled, the entire assembly is orientated vertically with the barbs (325) of the plunger (300) pointing down and the open end of the syringe barrel (410) pointing up. The interior of the syringe barrel is then filled with the liquid (425) up to a point generally level with the flat center line of the rupture disk seal (520).

Figure 5:
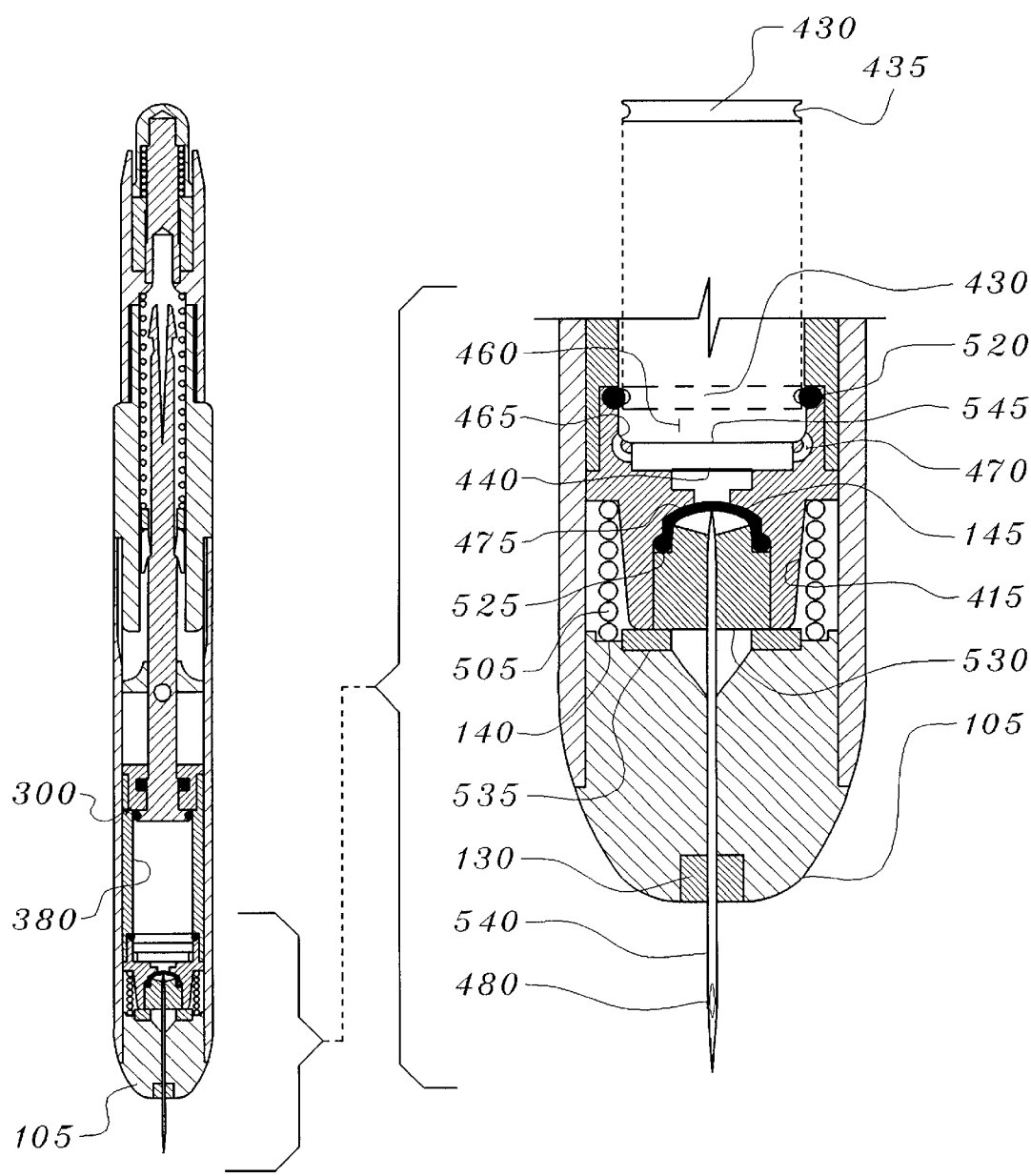
FIG. 5 describes the device as the plunger, syringe, and needle assembly is urged axially into a state where the leading end of the plunger, syringe, and needle assembly comes to rest at the stationary end of the housing and prior to the rigid disk separating from its seal.
Figure 6:
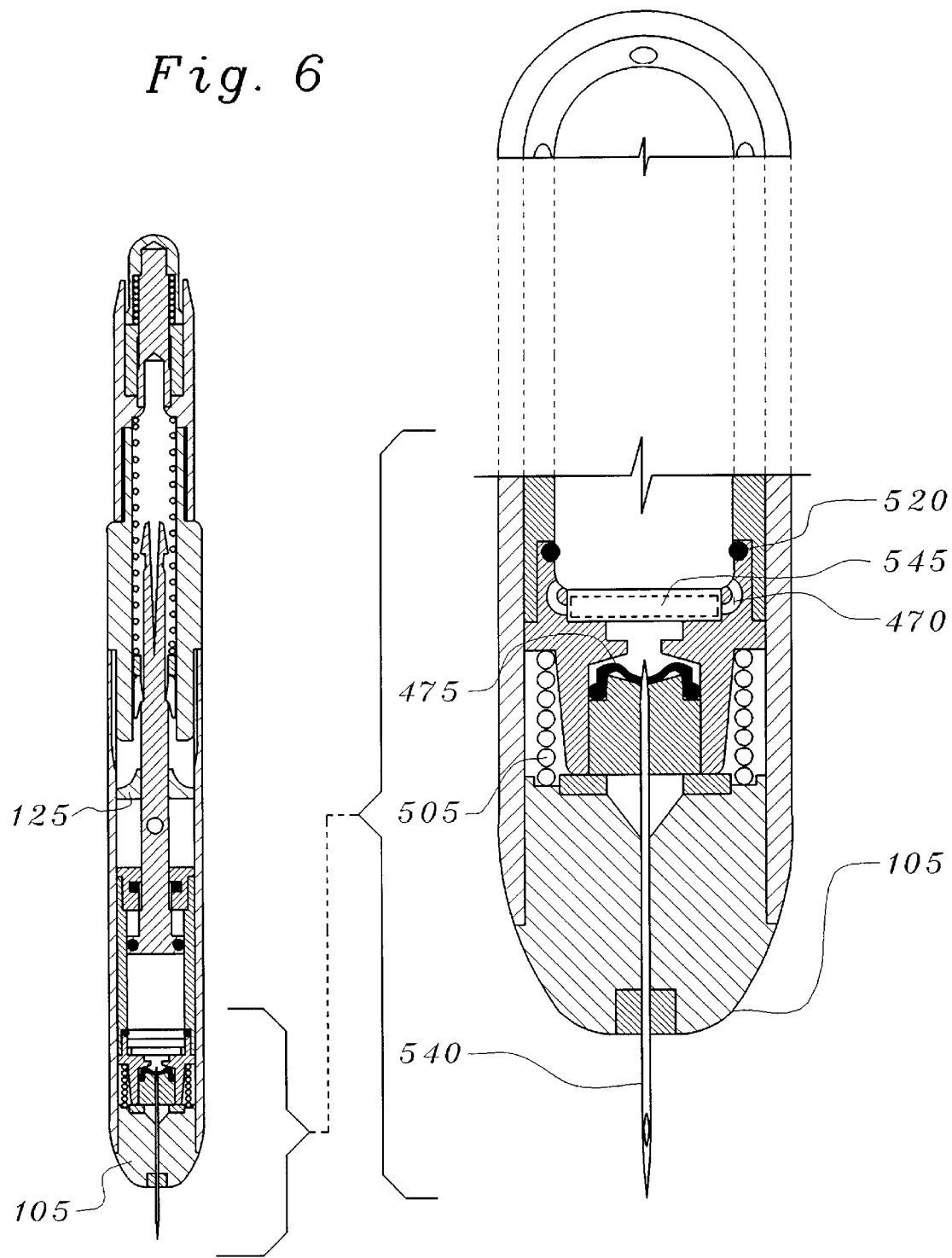
FIG. 6 describes the device as the rigid disk is fully separated from the circumferential seal, the lower drug chamber seal has been penetrated, and as the plunger has commenced its relative movement in relation to the syringe assembly.

Referring to FIG. 5 and 6, the rupture disk (430) is a thin, generally disk-shaped, non-porous element fashioned with a circumferential groove (435) about its periphery. This circumferential groove (435) is shaped and dimensioned to achieve a secure and elastic interference fit with the disk seal (520) so that the rupture disk seal (520) fits within the peripheral groove (435) of the rupture disk (430) and achieves a compressive fit with it. During assembly, the rupture disk (430) is secured into a compressive, circumferential fit with the rupture disk seal (520) after the rupture disk seal (520) is mounted into position in its designated location within the distal end of the plunger (300) and syringe (400) assemblies and after the syringe barrel (410) is filled with liquid (425). By securing the rupture disk (430) into place within the interior periphery of the rupture disk seal (520) while the rupture disk seal (520) is confined on its exterior within the counterbored pocket (450) of the syringe barrel (410), the rupture disk (430) and disk seal (520) form a fluid-tight barrier preventing air from entering the liquid while also preventing liquid from escaping the syringe barrel.

Once the syringe barrel (410) is loaded with liquid (425) and the rupture disk (430) is assembled with the rupture disk seal (520), the interference fit between the rupture disk exterior and the rupture disk seal interior is adequate to prevent separation of the two under axial loading of the rupture disk until a minimum threshold force is achieved. Assuming the liquid may be generally described as an incompressible fluid, and fluid pressure is applied symmetrically and evenly distributed across the proximal surface of the rupture disk, the internal pressure necessary to separate the rupture disk from the disk seal would be predictable. Once the first chamber is loaded with liquid (425), and the rupture disk (430) is installed, the preferred embodiment may be orientated in any direction.

Separation of the rupture disk (430) from the rupture disk seal (520) occurs at a pressure greater than created by the plunger (300) acting upon the liquid (425) during the free acceleration of the plunger (300) and syringe assembly (400) under the influence of a fully energized driver spring (500). Only after the pressure within the liquid exceeds a predictable threshold under the influence of the plunger (300) will the rupture disk (430) separate from the rupture disk seal (520) and the liquid (425) enter the second, dry drug chamber (460).

As shown in FIG. 5, the lower syringe cap (415) comprises a non-porous element having a proximal cavity to preferably contain a filter (440) and an optional dry or lyophilized medicine (545) and a distal cavity to contain a drug chamber lower seal (525) and a needle hub (530). Once the filter (440) and optional lyophilized medicine (545) are assembled within the proximal cavity of the lower syringe cap (415), the proximal end of the lower syringe cap is fitted within, and is permanently attached to, the distal end of the syringe barrel (410). The lower syringe cap (415) fits within the counter bore in which the rupture disk seal (520) and rupture disk (430) reside. When fully engaged with the syringe barrel (410), the radial surface of the lower syringe cap (415) compresses in the proximal direction against the rupture disk seal (520) and prevents axial movement of the rupture disk seal (520) in the distal direction. The proximal cavity of the lower syringe cap (415) is fashioned to provide a flat surface (465) on which the rupture disk (430) comes to rest when the liquid pressure exceeds the threshold level necessary to separate the rupture disk (430) from engagement with the rupture disk seal (520). The radially disposed interior surface (465) is slightly larger in diameter than outside diameter of the rupture disk (430). At least one aperture (470) across that interior surface (465) is fashioned into the lower syringe cap to allow the liquid to flow past the rupture disk (430) when the rupture disk resides in flat contact with interior surface (465) of the lower syringe cap (415). When the rupture disk (430) resides in this position, the dry drug chamber is effectively divided into a distal portion and a proximal portion, as shown in FIG. 5.

Referring to FIG. 5, a needle (540) is permanently bonded in an axial relationship to a needle hub (530). During final assembly of the syringe (400), an elastomeric drug chamber lower seal (525), which comprises a dome-shaped septum (475) is inserted septum end first into the distal cavity of the lower syringe cap (415) in an axial, proximal direction, until the disk-shaped compression surface of the drug chamber lower seal (525) seats against the receiving surface within the distal cavity of the lower syringe cap (415). Just prior to inserting and seating the drug chamber lower seal (525), the air within the interior of the dry drug chamber (460) (which comprises the space interior to the proximal cavity of the lower syringe cap (415) and enclosed on one end by the rupture disk (430) and on the other end by the drug chamber lower seal (525)), is preferably evacuated.

Once the drug chamber lower seal (525) is installed, the needle (540) and needle hub (530) are then inserted, and permanently affixed into, the lower syringe cap (415), so as to sandwich and compress the sealing surface of the drug chamber lower seal (525) between the flat radial surfaces of the lower syringe cap (415) and the needle hub (530). Once assembled, the proximal end of the needle (540) is positioned close to the concave surface of the drug chamber septum (475). While remaining in an evacuated state, the vacuum within the dry drug chamber (460) pulls the septum (475) of the dry drug lower seal (525) to rest against the distal interior surface of the lower syringe cap (415) so that the only surface on which the vacuum pressure acts is that exposed to the aperture leading from the dry drug chamber (460) to the distal cavity of the lower syringe cap (415).

Referring to FIGS. 1 and 5, at the distal end of the preferred embodiment, the sharp, tissue-penetrating distal end (480) of the needle (540) resides interior to, and in close proximity to, the septum of an elastomeric needle point seal (130). The needle point seal (130) comprises a cylindrical body and a hollow cavity sized slightly larger than the outside diameter of the needle that is open on the proximal end and closed by a thin septum on the distal end. The needle point seal (130) is permanently bonded into a receiving cavity at the distal-most end of the housing nose (105). The needle point seal (130) serves to protect the needle (540) from contamination by sources exterior to the device.

Again referring to FIGS. 1 and 5, the syringe return spring (505) is compressed slightly and positioned so that its axis generally aligns with the long axis of the housing (100). The distal end of the syringe return spring (505) rests upon a radially disposed interior surface (140) of the housing nose (105) and radially exterior to the impact damper pad (535). The proximal end of the syringe return spring (505) rests upon a radially oriented surface (145) proximal to the distal end of the lower syringe cap (415). In the absence of influence by the driver spring (500), the syringe return spring (505) urges the plunger (300) and syringe (400) combination proximally away from the housing nose (105) to a home position with the proximal surface of the upper syringe cap (405) resting against the distal surface (380) of coupling splitter (125). Referring to FIG. 5, the axial distance between the radially disposed and distally facing surface (145) of the lower syringe cap (415) and the interior surface (140) of the housing nose (105) is slightly greater than the solid height of the syringe return spring (505), measured when the distal surface of the lower syringe cap (415) is at rest upon the impact damper pad (535).

FIG. 1 shows the interrelationship between the various elements of the preferred embodiment, in a state of readiness. FIGS. 4 through 9 describe the various states of the device in the order of actuation sequence. FIG. 4 shows the device in an actuated state. FIG. 4 shows an enlarged detail of the proximal end of the device. FIG. 4 shows the actuation button (205) and actuation button rod (210) in an actuated relationship with the energized actuation button return spring (215), the actuation button retainer cap (220), the housing cap (120) and the barbs (325) of the plunger (300). In this view, the actuation button (205) and the actuation button rod (210) are shown at the terminus of their distal travel. Here the barbs (325) of the plunger (300) are shown channeled into the interior bore (270) of the actuation button rod (210).

In FIG. 4, the barbs of the plunger are shown compressed radially inward by the distal movement of the actuation button (205) and the actuation button rod (210) against the tapered surface (345) of the barbs (325). Axial and distal movement of the actuation button rod (210), which is attached to the actuation button (205), defeats the elastic forces urging the two halves of the barbs (325) of the plunger (300) apart. Continued axial and distal movement of the actuation button (205) and actuation button rod (210) relative to the housing cap (120), under the influence of the force imposed on the actuation button (205) by the user, reduces the physical interference between the plunger barbs (325) and the proximal surface of the aperture (265) in the housing cap (120), until, as the actuation button (205) and actuation button rod (210) approach the limit of their axial travel in the distal direction, the physical interference between the plunger and the housing cap ceases.

FIG. 4 thus represents the state when the interference between the plunger (300) and housing cap (120) stops, and just before the plunger (300) begins its acceleration in the distal direction, urged by the fully energized driver spring (500).

FIG. 5 shows the plunger (300) and syringe (400) combination at the end of its travel in the distal direction, where the distal end of the syringe assembly comes to rest against the impact damper pad (535). At this point, the needle (540) is exposed to the furthest extent achievable beyond the distal end of the housing nose (105). As the plunger (300) and syringe (400) combination traverses the distance from its origin to this location, the syringe return spring (505), which is substantially weaker than the driver spring (500), is compressed and gains energy.

As the plunger (300) is disengaged from its interference relationship with the housing cap (120), the fully energized driver spring (500), by virtue of its buttress contact at its proximal end with the interior face (255) of the housing cap (120), and its contact at the distal end at the proximal surface (385) of the spring-to-plunger coupling (340), forces the plunger (300) to accelerate in an axial direction away from the buttressed end of the driver spring (500). The spring-to-plunger coupling (340) is captured radially on its exterior by the interior surface of the interior bore (135) of the housing midsection (110), and radially on the interior by its disengagable interference relationship with the plunger groove (315). This cooperative relationship between the spring-to-plunger coupling (340), the housing midsection (110) and the plunger (300) assures the force of the driver spring (500) is directed to the plunger in a purely axial and distal direction and is guides the plunger (300) to travel with its center line coincident to the bore of the housing (100).

Once the plunger (300) and syringe (400) combination comes to rest upon the impact damper pad (535), the force applied to the plunger (300) by the driver spring (500) by means of the spring-to-plunger coupling (340) causes the pressure within the incompressible liquid (425) to rise rapidly, since the liquid (425) is trapped within the syringe barrel. The pressure within the syringe presses on all surfaces equally. As a result, the radial forces cancel each other and the force applied to the liquid (425) by the face (310) of the plunger (300) is transferred to the proximal surface of the rupture disk (430) residing in fluid contact. This pressure is directed in an axial, distal direction perpendicular to the fluid contact surface.

So long as the pressure differential between the proximal side of the rupture disk (430) and the distal side of the rupture disk does not exceed the threshold pressure necessary to dislodge the rupture disk (430) from its circumferential interference engagement with the rupture disk seal (520), the two elements remain engaged. Until the threshold force is exceeded, and the rupture disk separates from the rupture disk seal (520), the force applied to the plunger (300) by the driver spring (500) is applied to the syringe assembly (400) by means of the fluid pressure of the liquid (425) against the rupture disk (430), which in turn acts upon the rupture disk seal (520) that is trapped in axial engagement within the syringe assembly (400). The threshold pressure necessary to dislodge the rupture disk (430) from engagement with the rupture disk seal (520) is made greater than that generated by the plunger (300) acting upon the liquid (425) during the free travel of the syringe assembly (400). By design, the threshold force can only be exceeded once the syringe assembly comes to rest upon the impact damper pad (535) at the end of its allowable travel.

Under the influence of the plunger (300) upon the liquid (425) and the resistance to the imposed force by the securely-engaged rupture disk (430), the plunger (300), and syringe assembly (400) move in tandem in the distal direction. As the syringe assembly (400) begins to move, the distal end (480) of the needle (540) punctures the needle point seal (130) and enters the flesh at the injection site. FIG. 5 shows the preferred embodiment in a state where the needle (540) is fully extended as the syringe assembly (400) contacts the impact damper pad (535) and just prior to the rupture disk (430) separating from engagement with the rupture disk seal (520).

As described in FIG. 6, once the fluid pressure acting upon the rupture disk (430) of the preferred embodiment by the liquid (425) exceeds the threshold amount, the rupture disk (430) disengages from its circumferential interference relationship with the rupture disk seal (520) and moves distally a short distance into physical contact with a proximally-facing surface (465) of the lower syringe cap (415) within the proximal cavity of the lower syringe cap (415). The supporting surface (465) of the lower syringe cap (415) has an aperture (470) in at least one location, and preferably several locations, to allow the liquid (425) to flow around the rupture disk (430) and into the distal portion of the dry drug chamber (460) where, if the application calls for it, a dry medicine (545) resides.

Once the rupture disk (430) separates from the rupture disk seal (520) and the liquid (425) begins to flood the dry drug chamber (460), the vacuum being maintained within that compartment is broken and the volume within the unit is filled with the liquid (425). If therapeutic application calls for its use, the dry, highly soluble, medicine (545) residing within the dry drug chamber (460) would come into contact with the liquid (425) and rapidly begin to dissolve. Once the entire volume of the dry drug chamber (460) is filled with liquid (425), the pressure rises rapidly under the influence of the plunger (300) moving distally within the syringe barrel (410) and pressing upon the liquid (425). As the pressure rises within the dry drug chamber (460), the pressure of the liquid (425) causes the septum (475) of the drug chamber lower seal (525), to deflect distally.

As the septum (475) begins to deflect, it pulls away from the interior surface of the lower syringe cap (415) upon which it normally resides, and the surface area of the septum (475) exposed to the liquid expands. This increased surface area allows for an increasing force to act upon the septum (475), which in turn accelerates the distal deflection. The septum (475) eventually begins to invert as depicted in FIG. 6 and comes into penetrating contact with the proximal end of the needle (540), which is preferably beveled to facilitate penetration of the septum (475). When the pressure imposed upon the septum (475) of the drug chamber lower seal (525) exceeds a threshold, the septum (475) becomes fully penetrated by the stationary and securely fixed beveled end of the needle (540) and the liquid (425), possibly mixed with a dry medicine (545), begins to flow out of the needle (540) and into the recipient of the injection.

FIG. 6 depicts the preferred embodiment in a state where the rupture disk (430) is separated from engagement with the rupture disk seal (520), the dry drug chamber (460) within the lower syringe cap (415) is flooded with liquid medicine, the drug chamber septum (475) has been inverted and penetrated by the proximal end of the needle (540) and the plunger (300) is advancing distally causing the liquid medicine to flow through the needle (540) and into the recipient.

Figure 7:
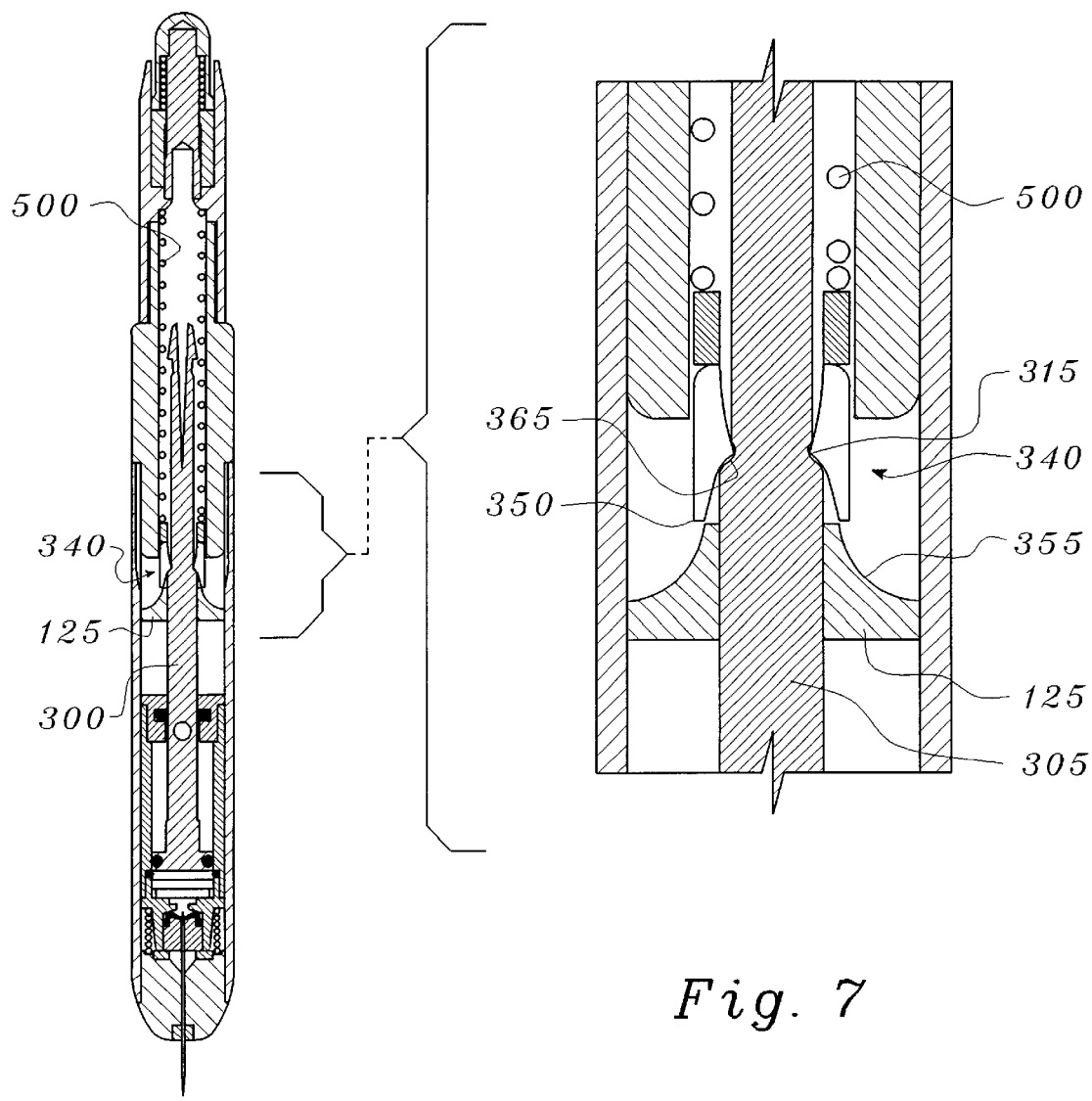
FIG. 7 describes the device when the plunger has moved forward, the injection liquid is almost entirely dispensed, and the leading end of the spring-to-plunger coupling has made contact with the surface of the disengaging element of the housing.

Referring to FIG. 7, as the plunger (300) of the preferred embodiment continues to move distally under the influence of the driver spring (500) by means of the spring-to-plunger coupling (340), the liquid medicine is expelled from the syringe assembly (400) through the needle (540) and into the recipient. As the plunger (300) approaches the distal end of the syringe barrel (410), the distal end (350) of the spring-to-plunger coupling (340) approaches the proximal end of the surface (355) of the coupling splitter (125). This surface (355) is generally sloping from the plunger shaft (305) to a lesser thickness; it may, for example, have a conical cross-section. FIG. 7 describes the state where the volume of liquid (425) dispensed is approaching the volume of the intended dose and spring-to-plunger coupling (340) has initiated contact with the coupling splitter (125).

Figure 8:
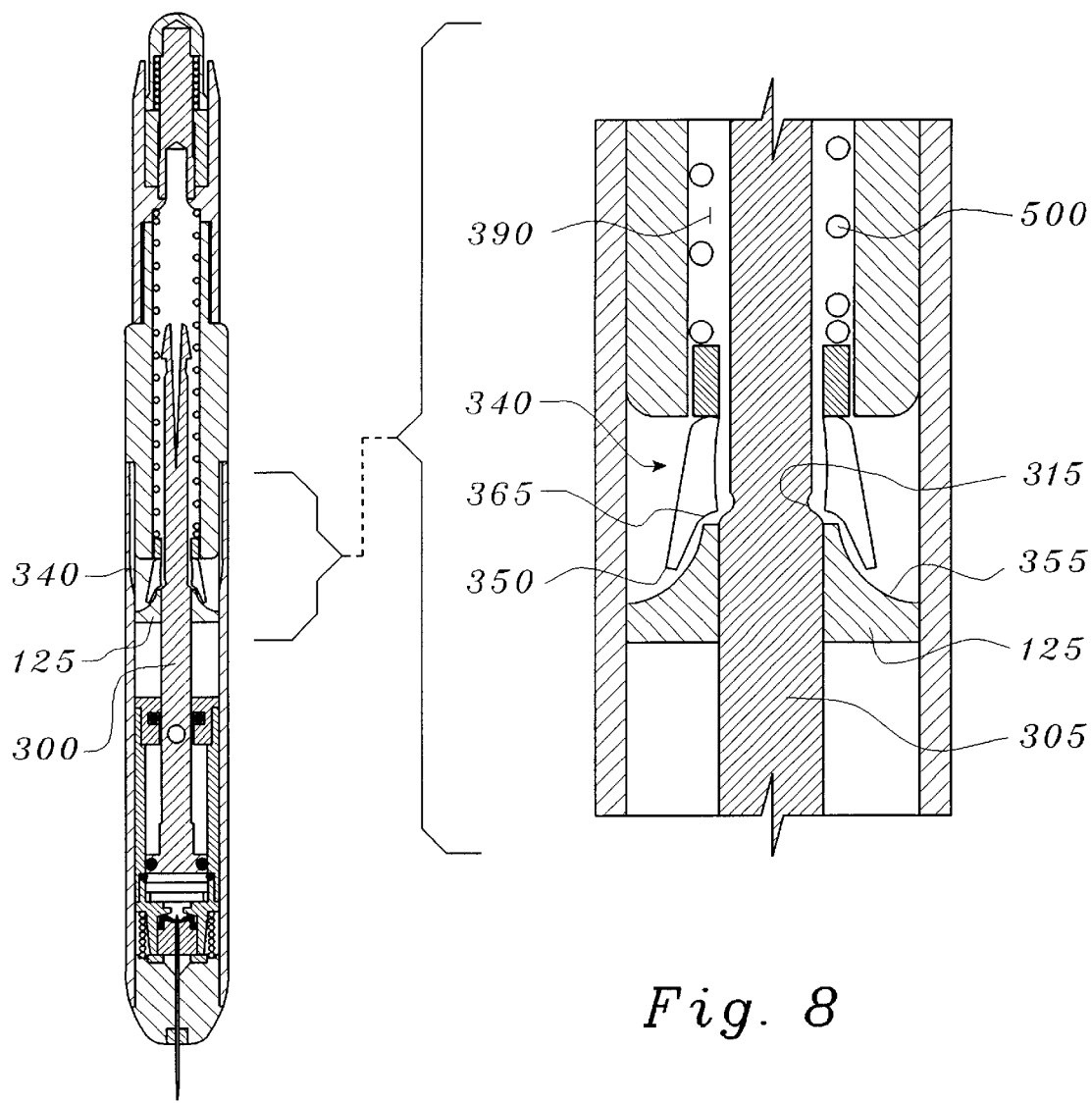
FIG. 8 describes the device as the spring-to-plunger coupling has fully opened and disengaged from the plunger, and the injection liquid has been entirely dispensed, but before the return spring has forced the plunger, syringe, and needle assembly rearward.

Referring to FIGS. 1 and 8, as the injection process nears its conclusion, the plunger (300) of the preferred embodiment continues to move distally under the influence of the driver spring (500) by means of the spring-to-plunger coupling (340) and the distal end (350) of the spring-to-plunger coupling (340) begins to ride over the sloping surface (355) of the coupling splitter (125). The spring-to-plunger coupling (340) is fabricated to include a plurality of axial slits (370) that are equally spaced around its periphery and extend from the distal end to a circumferential groove (360) around the spring-to-plunger coupling (340). The circumferential groove (360) serves to allow for easy flexure of the slotted portion of the spring-to-plunger coupling (340) in the radial direction at a known and axially consistent fulcrum point. The driver spring forces the distal portion (370) of the spring-to-plunger coupling (340) to ride over the surface (355) of the coupling splitter (125). As the slotted portion of the spring-to-plunger coupling (340) begins to open into a rosette pattern in a sliding relation to the sloping surface (355) of the coupling splitter (125), the degree of dimensional interference between the radial lip (365) of the spring-to-plunger coupling (340) and the corresponding groove (315) around the periphery of the plunger (300) diminishes until the engagement between the plunger (300) and the expanded spring-to-plunger coupling (375) ceases altogether.

FIG. 8 describes the state where substantially the entire volume of the liquid (425) has been dispensed, and spring-to-plunger coupling (340) has disengaged entirely from contact with the plunger (300). The driver spring (500) therefore has no further influence on the plunger (300) by way of the spring-to-plunger coupling (340). The interior bore (395) of the spring-to-plunger coupling proximal to the groove (360) is dimensioned to provide an easy slip fit with the shaft (305) of the plunger (300) once the interference relationship between the spring-to-plunger coupling (340) and the plunger (300) is terminated. The flow of medicine out of the syringe barrel (410) ends upon disengagement of the spring-to-plunger coupling (340) from the plunger (300). The plunger (300) and syringe (400) combination is now influenced only by the energized syringe return spring (505) acting upon the distally facing surface (145) of the lower syringe cap (415). FIG. 8 represents the state when the spring-to-plunger coupling has become disengaged from the plunger, and the flow of liquid out of the device has ceased, but the emptied plunger (300) and syringe (400) combination has yet to respond to the influence of the energized syringe return spring (505).

Figure 9:
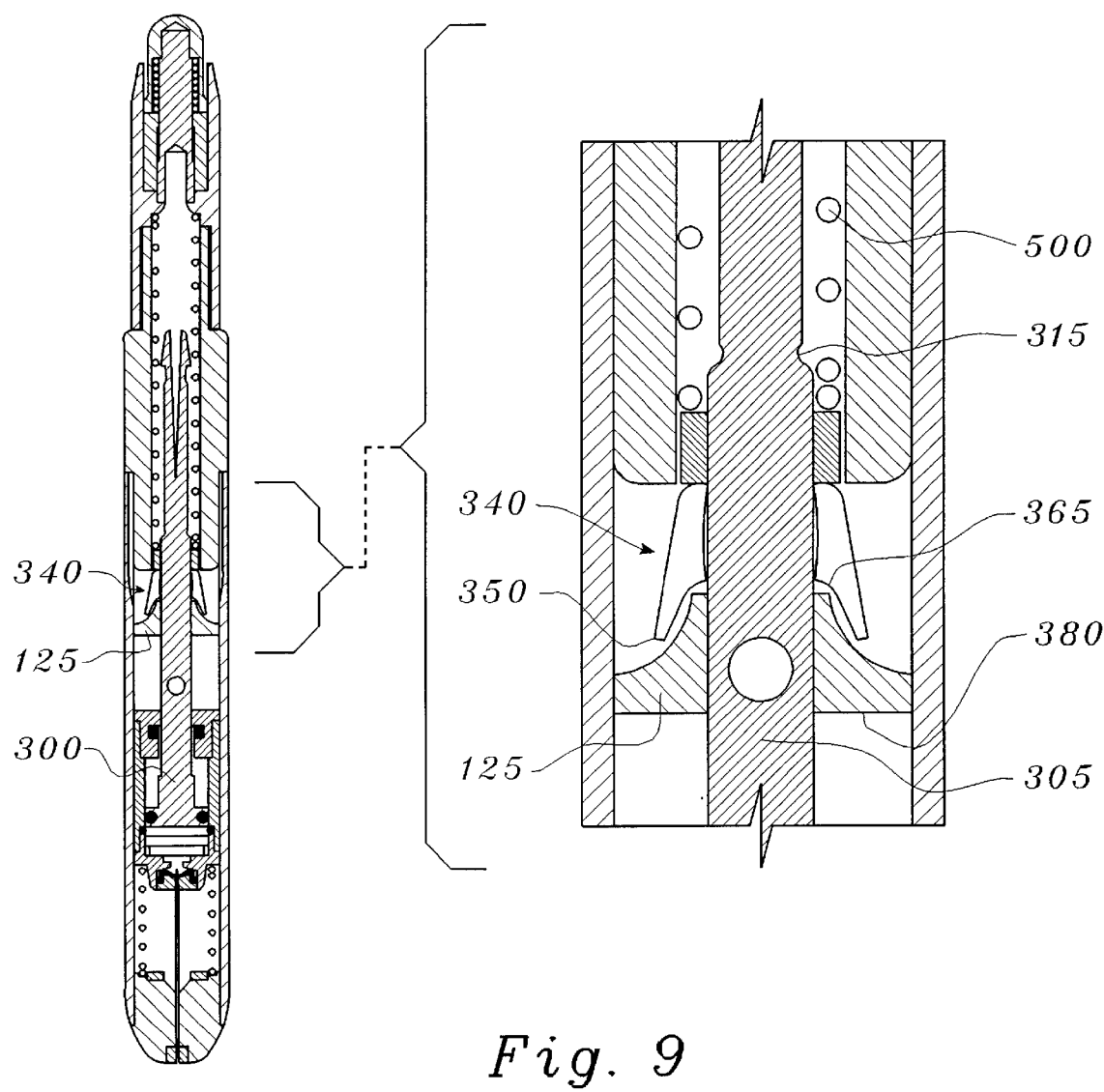
FIG. 9 describes the device when the injection process had completed, and the plunger, syringe, and needle assembly have fully retracted.

As depicted in FIG. 9, once the spring-to-plunger coupling (340) has been flared outward by its involvement with the coupling splitter (125) so as to end its engagement with the plunger (300), and the plunger (300) is therefore no longer urged distally by the driver spring (500), the energized syringe return spring (505) acts upon the lower syringe cap (415), and forces the plunger (300) and syringe (400) combination in a proximal direction. The plunger (300) and syringe (400) combination continues to accelerate in the proximal direction until the proximal surface of the upper syringe cap (405) contacts the distal surface (380) of the coupling splitter (125) at which time the distal end (480) of the needle (540) is fully retracted into the housing nose (105). The syringe return spring (505) remains in a moderately biased and energized state upon full retraction of the plunger (300) and syringe (400) combination.

The device is thus rendered harmless because there is no risk of exposure to the used hypodermic needle and the blood-borne diseases that may be transmitted through contaminated hypodermic needles. The device may then be disposed of by conventional means without risk of injury or infection to others who may come into contact with it. FIG. 9 thus represents the terminal state of the preferred embodiment after the injection process has been completed, the needle has been fully retracted, and the device has been rendered safe for disposal.

I claim:

1. An automatic mixing and injecting apparatus comprising:
   a. a housing having a cavity and a proximal and a distal end;
   b. a syringe assembly within the housing cavity, the syringe assembly further comprising:
      (1) a first chamber for holding a liquid;
      (2) a second chamber for holding a dry medicine, the second chamber disposed distally to the first chamber; the second chamber releasably sealed with respect to the first chamber;
      (3) a needle, the needle disposed distally of the second chamber; and,
      (4) a plunger; the plunger having a plunger shaft disposed proximally; the plunger being operable to force the liquid from the first chamber into the second chamber;
      (5) a spring-to-plunger coupling engaging the plunger shaft and the driver spring;
      (6) a splitter; the splitter attached to the housing distally to the spring-to-plunger coupling; the splitter further having a surface for engaging the spring-to-plunger coupling and forcing the spring-to-plunger coupling to disengage from the plunger shaft, thereby disengaging the driver spring from the syringe assembly; and,
   c. a driver spring within the housing, the driver spring engaging the plunger shaft, and operable when released to inject the needle and displace the liquid from the first chamber, through the second chamber and through the needle.

2. The automatic mixing and injecting apparatus of claim 1, where the plunger shaft further comprises a circumferential groove; and, the spring-to-plunger coupling further comprises:
   a. a plurality of axial slits; and,
   b. a radial lip for releasably engaging the circumferential groove, so that the radial lip disengages from the circumferential groove as the spring-to-plunger coupling engages the splitter.

3. The automatic mixing and injecting apparatus of claim 1, further comprising:
   a. a disk releasably sealing the first chamber from the second chamber; and,
   b. at least one aperture in the wall of the second chamber allowing liquid communication between the portion of the second chamber proximal to the released disk and the portion of the second chamber distal to the released disk, so that the liquid flows through the second chamber before being forced through the needle.

4. The automatic mixing and injecting apparatus of claim 1, further comprising a return spring; the return spring disposed between the housing and the syringe assembly; the return spring urging the syringe assembly proximally.

5. The automatic mixing and injecting apparatus of claim 1, further comprising:
   a. at least two compressible barbs; the barbs connected to the proximal end of the plunger shaft;
   b. the housing having a housing cap;
   c. a rod moveably disposed within the housing cap; the rod having an interior bore sized to receive the barbs in their compressed state; and,
   d. a detent integral with the housing cap; the detent sized to engage the barbs in their uncompressed state and prevent the distal movement of the plunger shaft until the barbs are compressed.

6. The automatic mixing and injecting apparatus of claim 1 further comprising a flexible septum; the flexible septum disposed proximally to the proximal end of the needle and sealing the needle from the second chamber; so that liquid pressure in the second chamber causes the septum to deflect distally until the septum is penetrated by the proximal end of the needle.

7. An automatic mixing and injecting apparatus comprising:
   a. a housing having a cavity and a proximal and a distal end;
   b. a syringe assembly within the housing cavity, the syringe assembly further comprising:
      (1) a first chamber for holding a liquid;
      (2) a second chamber; the second chamber disposed distally to the first chamber;
      (3) a disk releasably sealing the first chamber from the second chamber;
      (4) a needle disposed distally of the second chamber;
      (5) a plunger; the plunger having a plunger shaft disposed proximally; the plunger being operable to force the liquid from the first chamber and cause the disk to release;
      (6) a spring-to-plunger coupling engaging the plunger shaft and the driver spring;
      (7) a splitter; the splitter attached to the housing distally to the spring-to-plunger coupling; the splitter further having a surface for engaging the spring-to-plunger coupling and forcing the spring-to-plunger coupling to disengage from the plunger shaft, thereby disengaging the driver spring from the syringe assembly; and,
   c. a least one aperture in the wall of the second chamber allowing liquid communication between the portion of the second chamber proximal to the released disk and the portion of the second chamber distal to the released disk, so that the liquid flows through the second chamber before being forced through the needle.

8. The automatic mixing and injecting apparatus of claim 7, where the plunger shaft further comprises a circumferential groove; and, the spring-to-plunger coupling further comprises:
   a. a plurality of axial slits; and,
   b. a radial lip for releasably engaging the circumferential groove, so that the radial lip disengages from the circumferential groove as the spring-to-plunger coupling engages the splitter.

9. The automatic mixing and injecting apparatus of claim 7, further comprising a driver spring within the housing, the driver spring engaging the plunger shaft and operable when released to inject the needle and displace the liquid past the released disk, through the second chamber and through the needle.

10. The automatic mixing and injecting apparatus of claim 7, further comprising a return spring; the return spring disposed between the housing and the syringe assembly; the return spring urging the syringe assembly proximally when the driver spring is disengaged from the syringe assembly.

11. The automatic mixing and injecting apparatus of claim 7, further comprising:
   a. at least two compressible barbs; the barbs connected to the proximal end of the plunger shaft;

b. the housing having a housing cap;
c. a rod disposed within the housing cap; the rod having an interior bore sized to receive the barbs in their compressed state; and,
d. a detent integral with the housing cap; the detent sized to engage the barbs in their uncompressed state and prevent the distal movement of the plunger shaft until the barbs are compressed.

12. The automatic mixing and injecting apparatus of claim 7 further comprising a flexible septum; the flexible septum disposed proximally to the proximal end of the needle and sealing the needle from the second chamber; so that liquid pressure in the second chamber causes the septum to deflect distally until it is penetrated by the proximal end of the needle.

13. An automatic injecting apparatus comprising:
   a. a housing having a cavity and a proximal and a distal end;
   b. a syringe assembly within the housing, the syringe assembly further comprising:
      (1) a first chamber for holding a liquid;
      (2) a needle; and,
      (3) a plunger, the plunger having a plunger shaft disposed proximally, the plunger being operable to force the liquid from the first chamber;
   c. the plunger shaft engaging a spring-to-plunger coupling;
   d. a driver spring within the housing, engaging the spring-to-plunger coupling, operable to the syringe assembly to inject the needle and displace the liquid medicine through the needle; and,
   f. a splitter attached to the plunger shaft distally to the spring-to-plunger coupling; the splitter having a surface for engaging the spring-to-plunger coupling and forcing the spring-to-plunger coupling to disengage from the plunger shaft, thereby disengaging the driver spring from the syringe assembly.

14. The automatic injecting apparatus of claim 13, where the plunger shaft further comprises a circumferential groove; and, the spring-to-plunger coupling further comprises:
   a. a plurality of axial slits; and,
   b. a radial lip for releasably engaging the circumferential groove, so that the radial lip disengages from the circumferential groove as the spring-to-plunger coupling engages the splitter.

15. The automatic injecting apparatus of claim 13, further comprising:
   a. a second chamber for holding a liquid;
   b. a disk disposed between the first chamber and the second chamber; the disk releasably sealing the first chamber from the second chamber; and,
   c. a least one aperture in the wall of the second chamber allowing liquid communication between the portion of the second chamber proximal to the disengaged disk and the portion of the second chamber distal to the disengaged disk, so that the liquid flows through the second chamber before being forced through the needle.

16. The automatic injecting apparatus of claim 13, further comprising a return spring; the return spring disposed between the housing and the syringe assembly; the return spring urging the syringe assembly proximally when the driver spring is disengaged from the syringe assembly.

17. The automatic mixing and injecting apparatus of claim 13, further comprising:
   a. at least two compressible barbs; the barbs connected to the proximal end of the plunger shaft;

b. the housing having a housing cap;
c. a rod disposed within the housing cap; the rod having an interior bore sized to receive the barbs in their compressed state; and,
d. a detent integral with the housing cap; the detent sized to engage the barbs in their uncompressed state and prevent the distal movement of the plunger shaft until the barbs are compressed.

18. The automatic mixing and injecting apparatus of claim 13 further comprising a flexible septum; the flexible septum disposed proximally to the proximal end of the needle and sealing the needle from the second chamber; so that liquid pressure in the chamber causes the septum to deflect distally until the septum is penetrated by the proximal end of the needle.

19. An automatic mixing and injecting apparatus comprising:
   a. a housing having a cavity and a proximal and a distal end;
   b. a syringe assembly within the housing cavity, the syringe assembly further comprising:
      (1) a first chamber for holding a liquid;
      (2) a second chamber for holding a dry medicine, the second chamber disposed distally to the first chamber;
      (3) a disk releasably sealing the first chamber from the second chamber;
      (4) a needle, the needle disposed distally of the second chamber;
      (5) a plunger; the plunger having a plunger shaft disposed proximally; the plunger being operable to force the liquid from the first chamber into the second chamber;
      (6) at least one aperture in the wall of the second chamber allowing liquid communication between the portion of the second chamber proximal to the released disk and the portion of the second chamber distal to the released disk, so that the liquid flows through the second chamber before being forced through the needle;
   c. a driver spring within the housing, the driver spring engaging the plunger shaft, and operable when released to inject the needle and displace the liquid from the first chamber, through the second chamber and through the needle;
   d. a spring-to-plunger coupling engaging the plunger shaft and the driver spring;
   e. a splitter; the splitter attached to the housing distally to the spring-to-plunger coupling; the splitter further having a surface for engaging the spring-to-plunger coupling and forcing the spring-to-plunger coupling to disengage from the plunger shaft, thereby disengaging the driver spring from the syringe assembly;
   f. the plunger shaft further comprising a circumferential groove; and, the spring-to-plunger coupling further comprising:
      (1) a plurality of axial slits; and,
      (2) a radial lip for releasably engaging the circumferential groove, so that the radial lip disengages from the circumferential groove as the spring-to-plunger coupling engages the splitter;
   g. at least two compressible barbs; the barbs connected to the proximal end of the plunger shaft;
   h. a rod axially moveable within the housing; the rod having an interior bore sized to receive the barbs in their compressed state; and, i. a detent integral with the housing; the detent sized to engage the barbs in their uncompressed state and prevent the distal movement of the plunger shaft until the barbs are compressed;

j. a return spring; the return spring disposed between the housing and the syringe assembly; the return spring urging the syringe assembly proximally; and, k. a flexible septum; the flexible septum disposed proximally to the proximal end of the needle and sealing the needle from the second chamber; so that liquid pressure in the second chamber causes the septum to deflect distally until it is penetrated by the proximal end of the needle.

\* \* \* \* \*